United States Patent [19]

Freeman, deceased

[11] Patent Number: 4,552,019
[45] Date of Patent: Nov. 12, 1985

[54] METHOD AND APPARATUS FOR MEASURING A COLLOIDAL POTENTIAL

[75] Inventor: Mark P. Freeman, deceased, late of Darien, Conn., by Helen M. Freeman, executrix

[73] Assignee: Dorr-Oliver, Incorporated, Stamford, Conn.

[21] Appl. No.: 612,502

[22] Filed: May 21, 1984

[51] Int. Cl.[4] .................. D21F 7/06; D21F 11/00; G01N 27/26; G01N 29/00
[52] U.S. Cl. .................................. 73/584; 73/590; 162/198; 162/263
[58] Field of Search ............... 73/584, 590; 162/198, 162/263

[56] References Cited
U.S. PATENT DOCUMENTS 4,294,656 10/1981 Beck et al. ..................... 162/192
4,497,208 2/1985 Oja et al. ........................ 73/584

Primary Examiner—Howard A. Birmiel
Attorney, Agent, or Firm—Paul D. Greeley; Burtsell J. Kearns; Gary R. Plotecher

[57] ABSTRACT

A method and apparatus for measuring a colloidal potential are described using pulses of ultrasonic energy that are directed along a path within a liquid suspension of colloidal particles. A vibration potential is measured at at least a pair of positions along the path. The positions are known relative to the source of ultrasonic pulses. The vibration potential measurements are then used to derive a colloidal potential which is independent of its attenuation encountered by the ultrasonic energy inside the suspension. In one embodiment several potential measuring probes are used and in another embodiment one probe is moved between predetermined positions.

9 Claims, 2 Drawing Figures

METHOD AND APPARATUS FOR MEASURING A COLLOIDAL POTENTIAL

FIELD OF THE INVENTION

This invention generally relates to a method and apparatus for obtaining an indication of the magnitude of a colloidal potential in a liquid suspension of colloidal particles. More specifically this invention relates to a method and apparatus for obtaining such colloidal potential indication by using ultrasonic energy.

BACKGROUND OF THE INVENTION

In U.S. Pat. No. 4,294,656, by U. Beck et al., a suspension is exposed to a field of ultrasonics. A voltage or potential is then measured in the field with a pair of electrodes which are separated by a distance that is about an odd half multiple of the ultrasonic wavelength in the suspension. The measured potential can be regarded as a vibration potential that can be used to control for example the retention or addition of flocculating agents to the liquid suspension. A further description of the technique can be found in an article entitle: "Measuring Zeta Potential by Ultrasonic Waves", by U. Beck, R. Zana and E. Rohloff and published on September 1978 at pages 63-65 of a publication entitled Tappi, this publication being also identified in U.S. Pat. No. 4,294,656.

SUMMARY OF THE INVENTION

With a technique in accordance with the invention an improved measurement of a colloidal potential can be obtained from its exposure to a pulsed ultrasonic field. This involves a measurement of the vibration potential at at least several positions in an ultrasonic field within a colloidal liquid suspension with the distance between the positions and from the source of ultrasonic pulses being known. These measurements then are used to derive an indication of a colloidal potential which is not dependent upon the degree of attenuation of the sonic energy within the liquid suspension and can be rapidly and repeatably obtained.

It is, therefore, an object of the invention to provide a method and apparatus for measuring a colloidal potential utilizing ultrasonic energy.

This and other objects and advantages of the invention can be understood from the following detailed description of the invention as described in conjunction with the drawing.

DETAILED DESCRIPTION OF DRAWING

Figure 1:
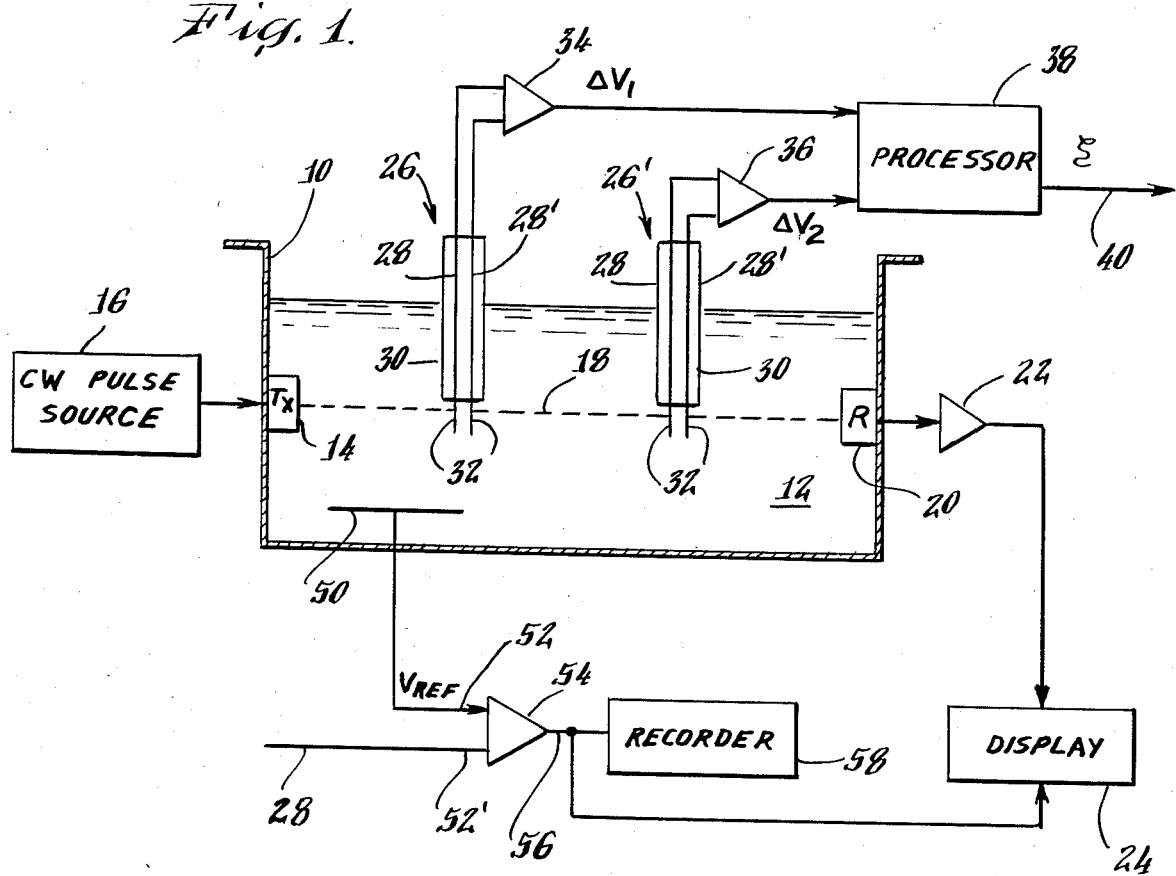
FIG. 1 is a schematic block diagram of an apparatus in accordance with the invention for use in deriving a measurement of a collidal potential.

With reference to FIG. 1, a tank or pipe 10 holds a liquid suspension 12 of colloidal particles such as fibers or the like. The liquid suspension may be such as for example is produced in a paper manufacturing process. Typically it is desired to enhance the removal of the particles such as with flocculating agents. Since the suspension may be continually changing it is desired to monitor a parameter such as a vibration potential to derive an indication of a colloidal potential. This latter potnetial is indicative of the ability of the particles to settle out with the aid of flocculating agents.

The tank 10 may be a chamber into which samples of the liquid suspension are placed or a pipe though which a portion of the suspension is diverted. An ultrasonic field is produced by an acoustic transmitting transducer 14, which is driven by a pulsed CW source 16. The frequency of the ultrasonic pulses is selected at a sufficiently high level to form a focused field of ultrasonic energy that travels along a path 18 inside the liquid suspension.

The ultrasonic pulses are detected by a receiver transducer 20 located at a known distance, d, from the transmitting transducer 14. The distance d may vary depending upon the amount of attenuation of the ultrasonic energy. The attenuation is a function of the nature of the liquid suspension 12 and the frequency of the ultrasonic energy with increased attenuation being associated with higher ultrasonic frequencies. The detected ultrasonic energy is applied to a controllable amplifier 22 and the magnitude of the signal displayed at a display 24. The received signal is used to confirm operation of the ultrasonic system and measure attenuation within the liquid suspension 120.

In the embodiment shown in FIG. 1, a pair of voltage sensing probes 26, 26' are shown submerged in suspension 12. Each probe 26 is formed of a pair of spaced apart leads 28, 28' which are encased in an insulating medium 30 such as glass except for their ends 32. The leads 28 are spaced apart by a distance which is selected to be approximately an odd half multiple of the wavelength of the ultrasonic frequency within the suspension. In practice this involves a separation of about one or several millimeters.

The probes 26, 26' are so positioned relative to the path 18 of the ultrasonic energy that they each can detect a vibration potential in the manner as disclosed in the aforementioned Beck et al. patent and publication. In addition, each probe 26 is positioned at a known distance $X_1$ and $X_2$ respectively from the acoustic transmitter 14 and thus also a known distance from each other. The vibration potentials sensed by each probe 26 are applied to amplifiers 34, 36 and then to a processor 38.

Processor 38, which may be a microprocessor, responds to the measured vibration potentials $v_1$ and $v_2$ to derive signals indicative of a colloidal potential, $\xi$, which is estimated to be an indication of the zeta potnetial. The colloidal potential is derived from the general relationships $$\Delta V_1 \sim \xi P_o E^{-kx_1}$$

$$\Delta V_2 \sim \xi P_o E^{-kx_2}$$

where $P_o$ is the initial amplitude of the pressure pulse introduced into the liquid suspension 12 by the pulsed actuation of transmitter 14; k is proportional to the attenuation in the liquid suspension of the acoustic pulse and $x_1$ and $x_2$ are the distances of the probes 26, 26' from the transmitter 14.

The pressure $P_o$ is a known quantity since it can be derived from a prior measurement conducted in, for example, a test liquid. The pressure $P_o$ may vary to some extent with different liquid suspensions because of the different acoustical impedance match between the transducer 14 and the suspension 12. However, some compensation can be provided by correspondingly altering the magnitude of the exciting electrical pulse from source 16.

The values $x_1$ and $x_2$ are the distances between the transmitter 14 and probes 26, 26' respectively. The distances $x_1$, $x_2$ may be set so that the probes 26 and 26' are approximately positioned at one-third and at two-third of the distance, d, between the transmitter 14 and receiver 20.

Accordingly, the value of a colloidal potential can be derived in processor 38 from the above two relationships which include two unknown factors using the well known simultaneous equations solving technique. The colloidal potential is provided on an output 40 in the form of a digital or analog signal. This may be recorded to provide information on the operation of a process.

Figure 2:
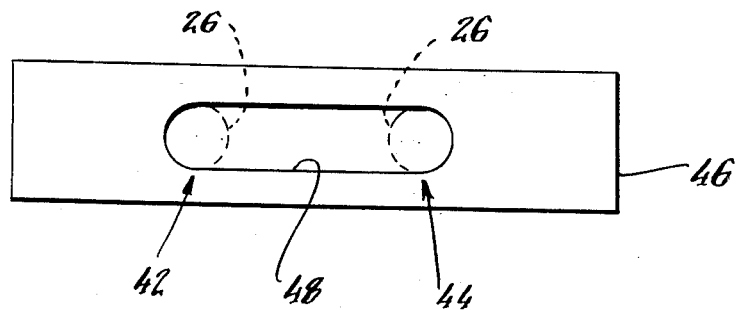
FIG. 2 is a top plan view of an alternate apparatus for deriving a measurement of a colloidal potential.

In an alternate form of the invention, a single probe 26 is used but moved between two positions such at 42 and 44 as shown in FIG. 2. The probe 26 is mounted on a slide 46 which has a slot 48 dispensed over a suspension container 10. The probe 26 can be precisely moved between positions 42, 44. When probe 26 is at position 42, the vibration potential is measured and a voltage corresponding thereto is recorded by processor 38. The probe is then moved to position 42' and the vibration potential measured and recorded for that position. The derivation of the colloidal potential may then be done as described above.

Since the polarity of the vibration potential is not obtainable from an ac measurement as made with probes 26, 26', a reference electrode 50 is submerged in the liquid suspension 12 at some distance from path 18 and is electrically coupled to one input 52 of a differential amplifier 54. One of the leads 28 or 28' of probes 26 or 26' is connected to the other input 52' of amplifier 54. The output 56 of amplifier is connected to a recorder 58 or applied to display 24 for display alongside the magnitude value of the colloidal potential. The polarity signal will only be applicable for the location of the lead 28 though similar measurements can be made for the other lead 28' of probes 26.

Having thus described an embodiment for determining a colloidal potential for a liquid suspension of colloidal particles the advantages of the invention can be appreciated. Variations from the described embodiments can be made without departing from the scope of the invention.

What is claimed is:

1. An apparatus for determining a colloidal potential of a liquid suspension of colloidal particles comprising:
   means for directing pulses of ultrasonic energy along a path within said liquid suspension;
   means for sensing a vibration potential at at least a first probe means and a second probe means, said first and second probe means each comprising a pair of electrodes, wherein said first and second probe means are separated from each other and from said pulse directing means by known predetermined distances, and each probe means producing signals indicative of said vibration potential at their respective positions; and
   means for combining said signals so as to derive an indication of a colloidal potential of said liquid suspension.

2. The apparatus as claimed in claim 1 and further comprising:
   means for detecting said ultrasonic pulses after their traversal through said suspension along a predetermined length of said path.

3. An apparatus as claimed in claim 2, wherein said first and second probe means are approximately positioned at one-third and at two-thirds of the predetermined length of the path between said means for directing pulses of ultrasonic energy and means for detecting said ultrasonic pulse, respectively.

4. An apparatus as claimed in claim 1, wherein said pair of electrodes are spaced apart by a distance of approximately an odd half multiple of the wavelength of the ultrasonic frequency.

5. An apparatus for determining a colloidal potential of a liquid suspension of colloidal particles comprising:
   means for directing pulses of ultrasonic energy along a path within said liquid suspension;
   a movable probe means for detecting a vibration potential along said path, said probe means being movable along said path between at least a first position and a second position, said probe means producing signals indicative of said vibration potential at said respective positions; and
   means for combining said signals so as to derive an indication of a colloidal potential of said liquid suspension.

6. The apparatus as claimed in claim 5 and further comprising:
   means for detecting said ultrasonic pulses after their traversal through said suspension along a predetermined length of said path.

7. An apparatus as claimed in claim 6, wherein said first and second positions of said movable probe means are at one-third and at two-thirds of the predetermined length of the path between said means for directing pulses of ultrasonic energy and means for detecting said ultrasonic pulses, respectively.

8. A method for determining a colloidal potential of a liquid suspension of colloidal particles comprising the steps of:
   directing pulses of ultrasonic energy along a path within said liquid suspension;
   measuring an electrical potential at at least a first probe means and a second probe means, said first and second probe means each comprising a pair of electrodes, wherein said first and second probe means are separated from each other and from said pulse directing means by known predetermined distances; and
   deriving from measured electrical potentials at said positions an indication of a colloidal potential of said liquid suspension.

9. The method as claimed in claim 8, wherein said measuring step further comprises the step of:
   detecting the ultrasonic pulses after their traversal through said suspension along a predetermined length of said path.

* * * * *